United States Patent [19]

Gregory et al.

[11] 4,033,329

[45] July 5, 1977

[54] MACHINE FOR DETERMINING VERTEBRAE LOCATIONS IN THE HUMAN BODY

[75] Inventors: Ralph R. Gregory; Peter Benesh, both of Monroe, Mich.

[73] Assignee: National Upper Cervical Chiropractic Research Association, Inc., Monroe, Mich.

[22] Filed: May 3, 1976

[21] Appl. No.: 682,518

[52] U.S. Cl. .............................. 128/2 S; 33/174 D
[51] Int. Cl.² ........................................... A61B 5/10
[58] Field of Search ................... 128/2 S; 33/174 D

[56] References Cited

UNITED STATES PATENTS

| | | | |
|---|---|---|---|
| 2,021,566 | 11/1935 | Millard | 128/2 S X |
| 2,111,648 | 3/1938 | Stone | 33/174 D |
| 2,324,672 | 7/1943 | Bierman et al. | 128/2 S X |
| 2,810,964 | 10/1957 | Engelbert | 33/174 D |
| 2,930,133 | 3/1960 | Thompson | 33/174 D |
| 3,027,761 | 4/1962 | Lauro | 33/174 D |
| 3,336,917 | 8/1967 | Pile et al. | 128/2 S |
| 3,575,159 | 4/1971 | Pile et al. | 128/2 S |
| 3,955,285 | 5/1976 | Moeckl | 33/174 D |

*Primary Examiner*—Kyle L. Howell
*Attorney, Agent, or Firm*—Harness, Dickey & Pierce

[57] ABSTRACT

The machine of the present invention measures and records in terms of the orientation planes of motion the presence of, the location of and the severity of the distortion-stress effects of C-1 subluxations on the human body, making possible thereby statistical analyses of reciprocal relationships between C-1 misalignments (determined by X-ray analysis) and such distortion-stress effects on the skeletal framework as directly result from the misalignment interferences of C-1 on the nervous system and its normal functioning. The machine can demonstrate the distortion-stress effects of a C-1 subluxation on the spine by checking the malpositional relationships of key vertebral segments along the spine prior to and subsequent to C-1 correction, indicating thereby the corrections obtainable throughout the spine and thus reducing the need for repeated applications of X-radiation to the patient. The machine has movable elements which provide indications of corrections or displacement and has a pair of vertically movable platforms with horizontally adjustable pads on which the patient stands. The pads are individually or simultaneously adjustable toward and away from each other to properly space the feet relative to the ilii. Either of the platforms may be elevated if a "short leg" is indicated, short leg being referred to hereinafter as "contractured leg."

17 Claims, 6 Drawing Figures

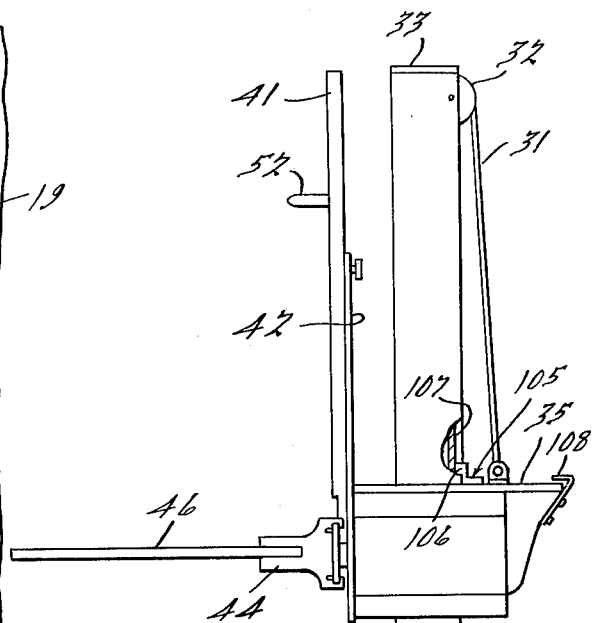
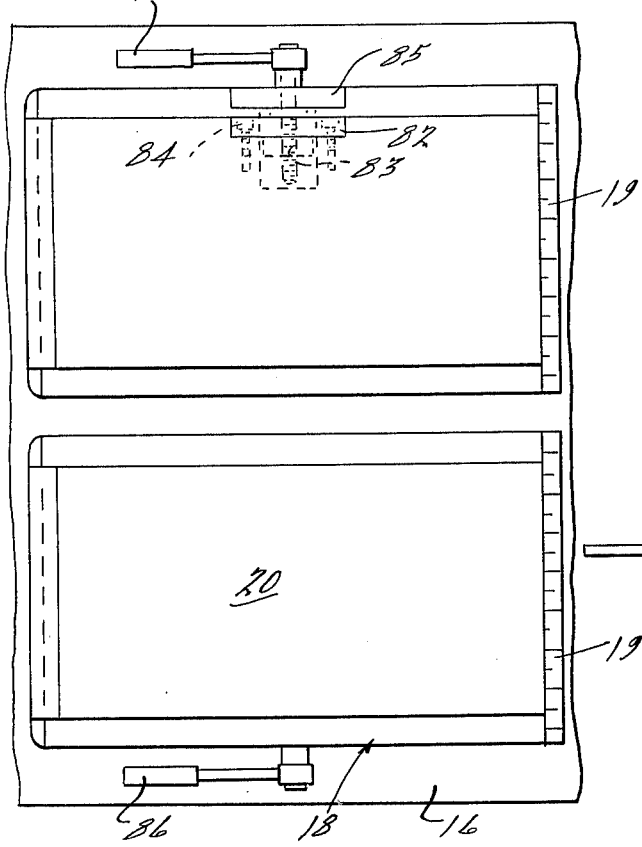
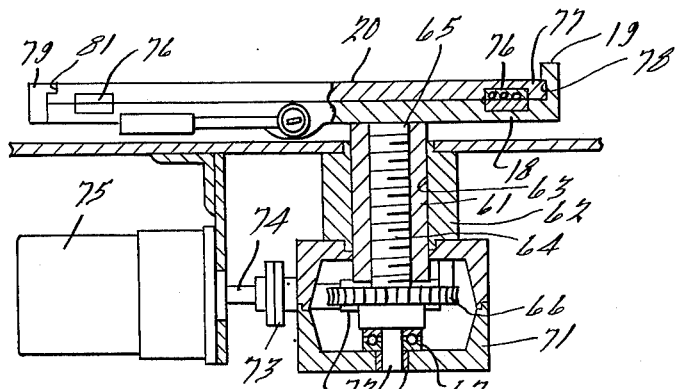
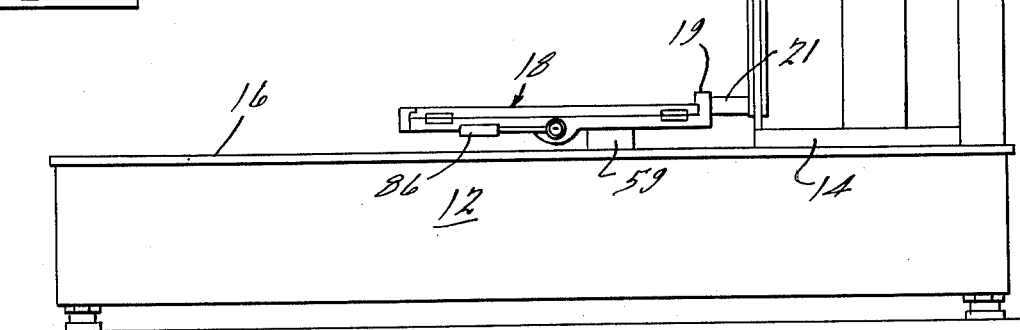

MACHINE FOR DETERMINING VERTEBRAE LOCATIONS IN THE HUMAN BODY

BACKGROUND OF THE INVENTION

In a search made on a machine the following list of patents was uncovered over which the present machine distinguishes in a patentable manner: U.S. Pat. Nos. 2,021,566; 3,027,761; 2,111,648; 3,196,551; 2,810,964; 3,336,917; 2,930,133.

SUMMARY OF THE INVENTION

The invention pertains to a machine which has a hollow base and a vertical column at one end. Forwardly of the column a pair of platforms are mounted for the feet of the patient who stands thereon. The platforms are adjustable toward and from each other and either is raisable relative to the other. The platforms have a fixed finger which is connected to pivoted horizontal arms on an upright having a scale across which the upward extension of the arms move to indicate the degree to which one or the other platform was raised. A cylindrical sleeve is mounted on the column for up, down and angular movement thereon with the column having a weight therein connected to a cable which passes out at the top over a counterbalancing wheel with the end connected to the transverse plane indicator which is secured to the top of the cylindrical sleeve. A transverse plate is mounted on the cylindrical sleeve in fixed relation thereto having a pelvic vernier bar pivoted thereto at its center. The bar carries a pair of laterally adjustable housings from which pivoted pelvic arms extend forwardly to engage the ilii of the patient, the spacing of which indicates the degree to which the feet of the patient should be spread apart. The pelvic arms may be adjusted from forward position illustrated to a position 45° and 90° therefrom to be retained in either position by a lever which locks the arms after adjustment. A scale at each end of the fixed arm designates the position in the frontal plane of the pelvic vernier bar.

A pillar extends upwardly in rear of the vertical column on the top of which a pair of spaced switches are mounted for energizing the motor on either one of the platforms in case a contractured leg is indicated so this may be raised to produce a balance to the patient which is indicated in the frontal plane or on the transverse plane if rotation simultaneously occurs. Each platform has a pad thereon in the nature of plates having adjustable means thereon for moving the pads toward and away from each other to space the feet of a patient standing on the platforms in accordance to the reading of the spacing of the arms which engage the ilii. The machine also has a vertebral probe slide bar extending upwardly from the transverse plate fixed to the cylindrical sleeve which has a slideway therein for a vertical probe which may be moved to key vertebrae in the spinal column and checked for displacement from the vertical axis. The angle of displacement of such key vertebra may be obtained on a scale on an upright portion on the fixed transverse plate.

BRIEF DESCRIPTION OF THE DRAWINGS

FIG. 4 is a side elevational view of the machine illustrated in FIG. 1;

FIG. 5 is a plan view of the platform portion of the structure illustrated in FIG. 2, and FIG. 6 is a sectional view of the structure illustrated in FIG. 2, taken on the line 6—6 thereof.

DESCRIPTION OF THE PREFERRED EMBODIMENT

Figure 1:
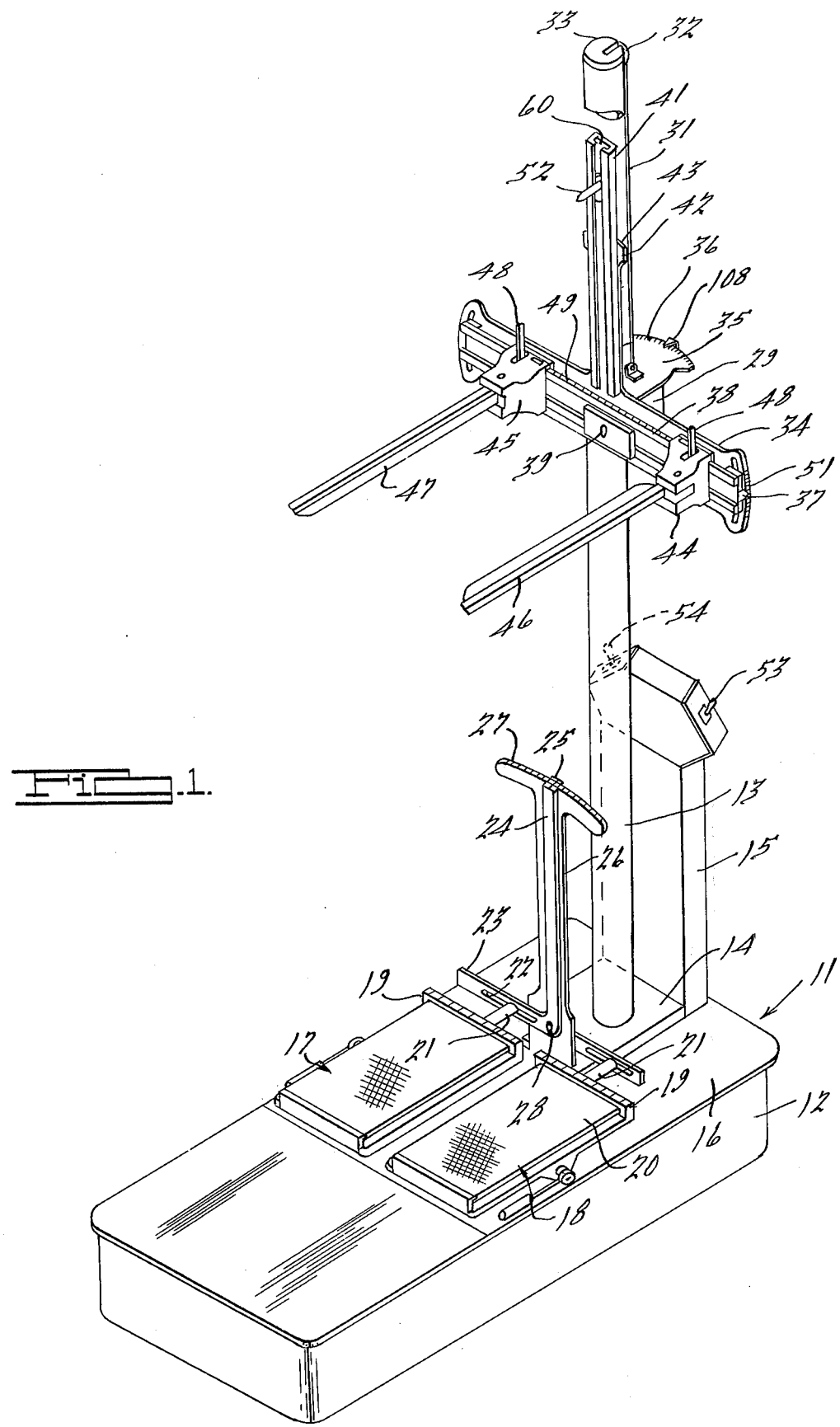
FIG. 1 is a perspective view of a skeleton checking machine embodying features of the present invention.
Figure 2:
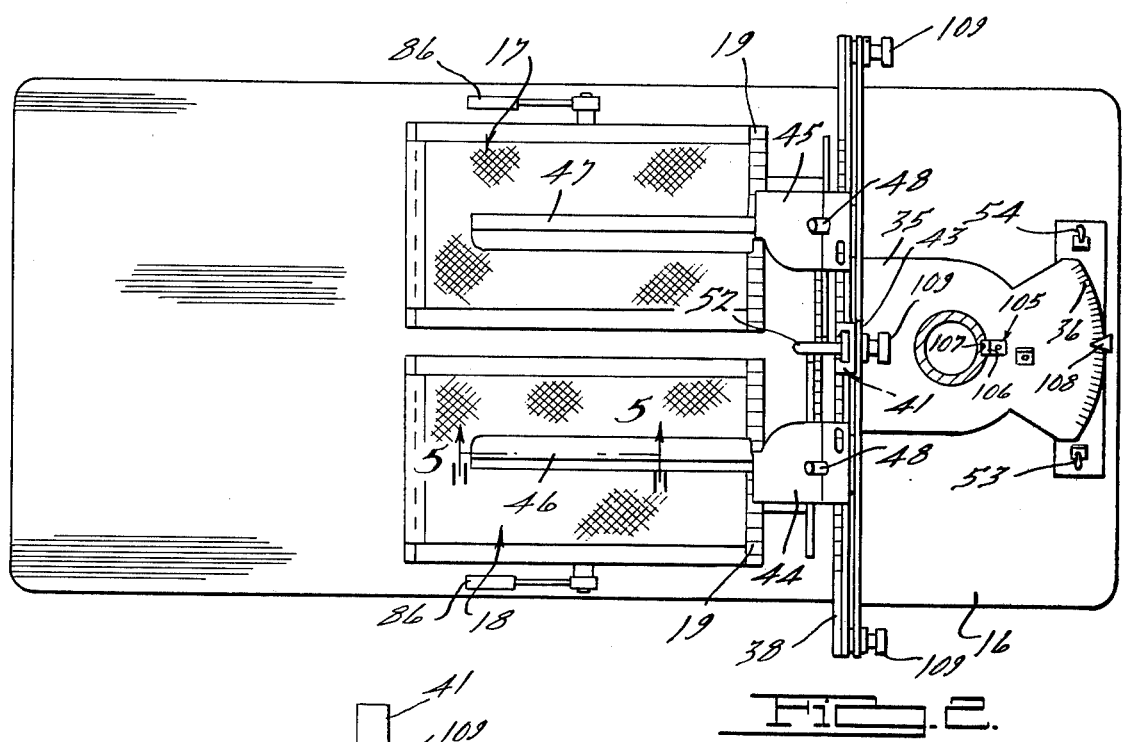
FIG. 2 is a plan view of the machine illustrated in FIG. 1.
Figure 3:
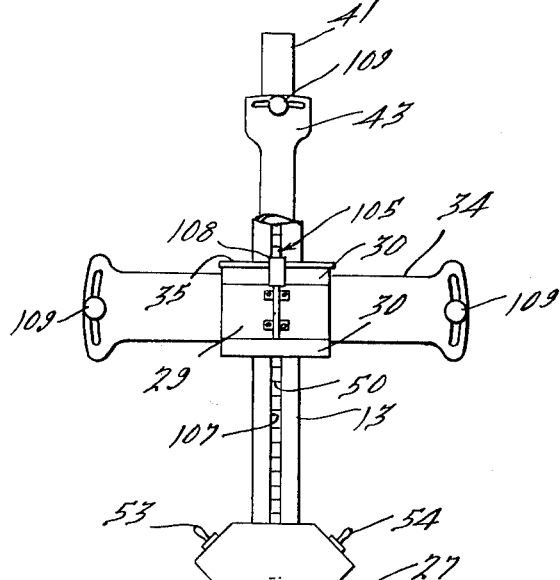
FIG. 3 is a rear view of the machine illustrated in FIG. 1.

The machine 11 has a base 12 from which a vertically extending column 13 is supported and reinforced by a plate 14 which engages an upright pedestal 15. A top plate 16 is secured to the top of the base 12 and a pair of platforms 17 and 18 are disposed thereabove for individual movement up and down in the vertical plane. Pads or plates 20 are mounted on the platforms 17 and 18 for lateral movement thereon toward and away from each other in the horizontal plane. The platforms 17 and 18 have heel-positioning flanges 19 at the rear thereof for locating the body of a patient relative to the machine. Actuating rods 21 are secured in fixed position to the rear end of the platforms having an end portion extending in a slot 22 in horizontal portions of L-shaped elevating registering arms 23. The vertical portions 24 and 25 of the arms are disposed on opposite sides of a fixed vertical plate 26 having a scale 27 from which readings may be taken to show the height to which either platform was raised. The L-shaped arms are secured to the bottom of the plate 26 by pivot means 28.

A hollow cylindrical sleeve 29 slides up and down on the column 13 and is rotatable thereabout. The sleeve is counterbalanced by a cable 31 which extends over a counterbalancing wheel 32 and secured to a weight (not illustrated) within the column. The wheel 32 is mounted on an angularly movable cap 33 located in the top of the column 13. A transversely disposed fixed plate 34 is secured to the sleeve 29 and is movable vertically and angularly therewith. A vertically movable transverse plane indicating plate 35 has a scale 36 thereon by which the amount of angular movement may be indicated by a finger 108 secured to the rotatable sleeve 29. The indicating plate 35 has an angle element 105 secured thereto with the upstanding end 106 disposed within a vertical slot 107 in the column 13 which prevents the plate 35 from turning. The cylindrical sleeve 29 is supported between spaced rings 30 of the plate 35 for angular movement about the column 13. The finger 108 secured to sleeve 29 indicates the amount of angular movement of the sleeve and plate 34 as indicated on the scale 36. The fixed plate 34 has a cross bar 38 secured thereto by a pivot 39 midway between the ends thereof. The pivot 39 also secures a vertebral probe slide bar 41 thereon forwardly of an upward extending vertebral indicator 42 which has a scale 43 thereon.

Right and left-handed housings 44 and 45 are mounted on the cross bar 38 for movement toward and away from each other and also angularly in the horizontal plane. The housings 44 and 45 have pivoted pelvic arms 46 and 47 which are mounted thereon for angular movement in a horizontal plane to extend in parallel relation, as illustrated in the Figures, or at 45° or 90° therefrom in which positions they can be locked by the pelvic arm lock levers 48 which are moved angularly toward the rear when in locked position. The arms 46 and 47 are movable toward and away from each other and upwardly and downwardly with the sleeve 29 to reach a position where they rest upon the ilii of a patient giving a space reading on the scale 49 on the top of the cross bar 38. From the scale readings, the pads 20 on each of the platforms 17 and 18 are adjusted toward or away from each other to have the feet of the patient separated a distance which conforms to the spacing of the ilii. When measurement is made, the cross bar 38 may be tilted in the vertical plane so that a reading on the end pelvic scales 51 may be obtained from the finger 37 on the ends of the pivoted bar 38 to show the offset of the ilii in the vertical plane which usually includes a rotational distortion which may be read on the scale 36 of the plate 35. The height of the ilii may be read from the vertical scale 50 located within the slot 107 in the column 13.

The vertebral probe slide bar 41 has a vertebral probe 52 disposed therein for vertical movement in the slide recess 60. The bar 41 is secured on the pivot 39 and can move angularly to have the probe 52 follow the position of the vertebrae as it is moved upwardly and downwardly in the slide recess 60 of the bar 41. When the elevating scale 27 provides an indication that the contractured leg is present, the platforms 17 or 18 which support the leg is elevated. This is accomplished by operating the switch lever 53 or 54, as the case may be, to energize the motor 75 which drives a worm 56 to operate a worm wheel 66 which turns a screw 65 to raise and lower a nut 59 which is secured to the underside of the platforms 17 or 18, whichever is to be raised. As pointed out above, either of the platforms is moved upwardly and downwardly through the actuation of one or the other switch levers 53 or 54.

As illustrated in FIGS. 5 and 6, the platforms 17 and 18 with the pads 20 therein are secured on a nut 61 which is supported within an opening 63 in a sleeve 62. A lead screw 64 has a mating thread 65 with that on the cylindrical interior aperture of the nut 61. The lead screw 64 is secured to a worm wheel 66 which is mounted on a thrust bearing 67 with the extending end 68 disposed within a bronze bushing 69 in the supporting frame 71. A worm on a shaft 72 is driven through a coupling 73 from the shaft 74 of a motor 75 which is rotated in a forward or reverse direction by one of the switches 53 or 54. The operation of the motor and the lead screw 64 at a reduced speed through the worm and worm wheel drive slowly raises or lowers one or the other platform 17 or 18 to raise the leg when found to be contracted.

The pads 20 are mounted on bearing slides 76 at each end of the platforms 17 and 18, the one end 77 being confined in a slot 78 in the heel-positioning flange 19 with the other end secured by an L-shaped hold-down plate 79 which extends within a notch 81 in the opposite end of the pad 20. Each of the pads has a bracket 82 containing a threaded aperture 83 secured to the remote sides by screws 84. The lead screw is supported for rotation in a bracket 85 secured to the outer edges of the platforms to be actuated by a ratchet lever 86 to move the platforms a short distance toward and away from each other. Such movement positions the feet of the patient standing on the platform a predetermined distance apart conforming to the reading obtained for the spacing of the ilii by the arms 46 and 47. After the cross bar 38 and the slide bar 41 have been angularly adjusted, they may be secured in position by thumb screws 109.

The machine is unique in determining the absence or the degree of the presence of interference with nervous conduction at the spinal level of the top cervical vertebrae (C-1) as expressed in terms of bodily distortions. It determines whether an adjustment thereof is required. It measures the effectiveness of such adjustment immediately following such adjustment and the degree to which it is corrective and, on succeeding checks, the length of time the correction remains stabilized. The machine also measures the state of muscular and/or skeletal stress of the body and to what degree. It measures the degree of pelvic-girdle distortion into the lateral, sagittal, and the transverse planes (orientation) of motion so that relationships to the misalignments of C-1 into the lateral and transverse planes can be established and compared. The machine indicates the influence of fatigue, stress, and other debilitating factors on the body in terms of bodily distortions. It predicts the onset of a C-1 subluxation and indicates changes in the misalignments of a C-1 subluxation indicative of the need for correction vector changes in the adjustment and a reevaluation of the subluxation listing. The machine reduces the need for unnecessary X-ray exposure by providing a means by which to determine if a trauma suffered by the patient since the original X-rays were taken was sufficient to change the original subluxation listing. The machine can measure changes in the height of the crests of the pelvis before and after an adjustment of C-1 and record deviations of individual vertebral segments in relation to the pelvic-girdle, and the effects of a C-1 adjustment on such deviations. The machine suggests the absence or the presence of abnormal bone structure by mechanically balancing the body prior to an adjustment of C-1 and provides a measurable means of establishing patients' progress in terms of bodily distortion, positive evidence of improvement, no improvement, or regression. The machine provides a data retrieval system, based on measurement, for comparing the patient's symptoms with body stress and can indicate whether a C-1 subluxation has been reduced to 0° in all planes.

What is claimed is:

1. In a checking machine for skeletal structure, a base, a top plate for said base, a column extending upwardly from said top plate near one end of the base, a cylindrical sleeve on said column for moving upwardly and downwardly and angularly thereon, a fixed transverse plate on said sleeve for rotation and vertical movement therewith, a cross bar pivotedly secured to said plate forwardly thereof, a pair of slidable housings movable toward and away from each other on said cross bar, and arms secured to said housings and movable angularly from a horizontal plane to indicate tilt and movable laterally of each other to increase or decrease the distance therebetween.

2. In a checking machine as recited in claim 1, wherein a scale on the end of the fixed plate indicates the amount of tilt of the arms, housing and cross bar, and a scale on said sleeve indicating the degree of rotation thereof and of the plate which is fixed thereto about the column.

3. In a checking machine as recited in claim 1, wherein a vertical scale is provided along the column, and means on said cylindrical sleeve for indicating a point of elevation on the column scale.

4. In a checking machine as recited in claim 3, wherein a vertically disposed slide bar has its bottom end pivoted to the fixed transverse plate, a probe extending from the slide bar for vertical movement therealong, and a scale on an extension of the fixed transverse plate by which the angular position of the probe is obtained.

5. In a checking machine as recited in claim 4, wherein a vertical scale is provided upon the pivoted slide bar for indicating the vertical position of said probe.

6. In a checking machine as recited in claim 1, wherein a pair of vertically movable platforms are mounted above the top plate of the base for independent vertical movement and for movement in a horizontal plane toward and away from each other, a scale plate extending vertically from the base, swingable indicating arms pivoted to said scale plate, and arms interconnecting the swingable arms and platforms to provide a reading for the vertical movement of one platform relative to the other.

7. In a checking machine as recited in claim 6, wherein each platform has a horizontal scale to indicate the spacing of the feet of a patient when standing thereon for measurement therewith.

8. In a checking machine as recited in claim 7, wherein each platform is supported on a nut which is raised or lowered by individual motors operated through gear reduction units and lead screws for permitting one platform to be raised and lowered relative to the other.

9. In a checking machine as recited in claim 8, wherein a pedestal is mounted on the base top plate in rear of the column, and a pair of switches on the pedestal for operating the motors individually for producing the raising of one platform relative to the other.

10. In a checking machine as recited in claim 1, wherein a counterbalancing wheel is secured to a rotatable plug at the top of the column, a weight on the interior of the column, a cable extending over the wheel and secured to said weight and to the cylindrical sleeve for providing a counterbalance therefore.

11. In a checking machine as recited in claim 10, wherein the arms on the housings are pivoted thereto so as to be movable from a position of parallelism to a position 45° and 90° therefrom, and locking means for securing the arms in the various adjustable positions.

12. In a checking machine as recited in claim 2, wherein said scale is provided on the edge of a plate which is counterbalanced and supports the cylindrical sleeve, means preventing the scale plate from rotating, and an indicator on said cylindrical sleeve which may rotate on said column.

13. In a checking machine as recited in claim 1, wherein said fixed transverse plate is fixed against rotation by projecting means which extends within a vertical slot in the column, supporting means between said transverse plate and sleeve which permits the sleeve to angularly move relative to the column, and a finger on said rotatable sleeve extending over a scale on said transverse plate to provide a reading for the rotation of said sleeve.

14. In a checking machine for skeletal structure, a base, a pair of vertically movable platforms supported on said base, pads on said platform movable in a horizontal plane toward and away from each other, a plate supported by said base adjacent to said platforms having a scale thereon, and indicating means operated by each platform relative to the scale for indicating the vertical movement thereof.

15. In a checking machine as recited in claim 14, wherein each platform has a scale to indicate the spacing of the patient's feet when standing on said pads.

16. In a checking machine as recited in claim 14, wherein each platform is supported on a nut which is raised or lowered by individual motors operated through gear reduction units and lead screws for permitting one platform to be moved vertically relative to the other.

17. In a checking machine as recited in claim 16, wherein a pedestal is mounted on the base, and a pair of switches supported by said pedestal for operating the motors individually for producing the independent vertical movement of the platforms.

* * * * *